(12) United States Patent
Fecher et al.

(10) Patent No.: US 11,964,058 B2
(45) Date of Patent: Apr. 23, 2024

(54) PROCESS FOR PREPARING NANOPARTICLES IN THE FORM OF A POWDER COMPRISING A BIO-RESORBABLE POLYESTER

(71) Applicant: EVONIK CORPORATION, Piscataway, NJ (US)

(72) Inventors: David Fecher, Saarbruecken (DE); Maria Camilla Operti, Darmstadt (DE); Rima Jaber, Frankfurt (DE); Andrea Engel, Birmingham, AL (US); Silko Grimm, Rossdorf (DE); Min Yang, Marlton, NJ (US)

(73) Assignee: Evonik Corporation, Piscataway, NJ (US)

( * ) Notice: Subject to any disclaimer, the term of this patent is extended or adjusted under 35 U.S.C. 154(b) by 0 days.

(21) Appl. No.: 17/754,327

(22) PCT Filed: Sep. 25, 2020

(86) PCT No.: PCT/EP2020/076853
§ 371 (c)(1),
(2) Date: Mar. 30, 2022

(87) PCT Pub. No.: WO2021/063813
PCT Pub. Date: Apr. 8, 2021

(65) Prior Publication Data
US 2022/0354803 A1 Nov. 10, 2022

(30) Foreign Application Priority Data
Oct. 1, 2019 (EP) ..................................... 19200713

(51) Int. Cl.
*A61K 9/51* (2006.01)
*C08J 3/16* (2006.01)

(52) U.S. Cl.
CPC .......... *A61K 9/5192* (2013.01); *A61K 9/5138* (2013.01); *A61K 9/5153* (2013.01); *C08J 3/16* (2013.01); *C08J 2367/02* (2013.01); *C08J 2367/04* (2013.01); *C08J 2467/04* (2013.01)

(58) Field of Classification Search
None
See application file for complete search history.

(56) References Cited

U.S. PATENT DOCUMENTS

2017/0354592 A1* 12/2017 Ivanova ............... A61K 9/0019
2018/0271782 A1 9/2018 Popov et al.

FOREIGN PATENT DOCUMENTS

| RU | 2637653 | 12/2017 |
|---|---|---|
| WO | 2004/026452 | 4/2004 |
| WO | 2015/024759 | 2/2015 |
| WO | 2015/181138 | 12/2015 |

OTHER PUBLICATIONS

Sergio Freitas, Gerhard Hielscher, Hans P. Merkle, and Bruno Gander. "Continuous contact- and contamination-free ultrasonic emulsification—a useful tool for pharmaceutical development and production." Ultrasonics Sonochemistry, vol. 13, 2006, pp. 76-85. (Year: 2006).*
Sergio Freitas, Beat Rudolf, Hans P. Merkle, and Bruno Gander. "Flow-through ultrasonic emulsification combined with static micromixing for aseptic production of microspheres by solvent extraction." European Journal of Pharmaceutics and Biopharmaceutics, vol. 61 2005, pp. 181-187. (Year: 2005).*
The NIST Reference on Constants, Units, and Uncertainty. https://physics.nist.gov/cuu/Units/units.html accessed Oct. 13, 2022, 5 printed pages. (Year: 2022).*
Solvent Miscibility Table. https://www.csustan.edu/sites/default/files/groups/Chemistry/Drake/documents/solvent_miscibility_table.pdf accessed Dec. 7, 2022, 1 printed page. (Year: 2022).*
Extended European Search Report dated Apr. 20, 2020 in European Patent Application No. 19200713.6, 5 pages.
Freitas et al., "Continuous contact- and contamination-free ultrasonic emulsification—a useful tool for pharmaceutical development and production", Ultrasonics Sonochemistry, vol. 13, 2006, pp. 76-85.
Freitas et al., "Flow-through ultrasonic emulsification combined with static micromixing for aseptic production of microspheres by solvent extraction", European Journal of Pharmaceutics and Biopharmaceutics, vol. 61, 2005, pp. 181-187.
International Search Report dated Dec. 16, 2020 in PCT/EP2020/076853, 6 pages.
Written Opinion dated Dec. 16, 2020 in PCT/EP2020/076853, 8 pages.
Operti et al.,"Industrial Scale Manufacturing and Downstream Processing of PLGA-Based Nanomedicines Suitable for Fully Continuous Operation", Pharmaceutics, vol. 14, No. 276, 2022, pp. 1-18. https://doi.org/10.3390/pharmaceutics14020276.
Operti et al., "Translating the Manufacture of Immunotherapeutic PLGA Nanoparticles from Lab to Industrial Scale: Process Transfer and in Vitro Testing", Pharmaceutics vol. 14, No. 1690, 2022, pp. 1-16. https://doi.org/10.3390/pharmaceutics14081690.

* cited by examiner

*Primary Examiner* — Isaac Shomer

(74) *Attorney, Agent, or Firm* — Grüneberg and Myers PLLC

(57) ABSTRACT

A process can be used for preparing nanoparticles containing at least one bio-resorbable polyester. The nanoparticles are in the form of a powder with a Z-Average particle size $D_z$ in the range of 1 to 450 nm, and with a polydispersity index PDI in the range of 0.01 to 0.5. The process involves emulsion-solvent extraction or emulsion-solvent evaporation, and application of ultrasonic sound.

21 Claims, No Drawings

PROCESS FOR PREPARING NANOPARTICLES IN THE FORM OF A POWDER COMPRISING A BIO-RESORBABLE POLYESTER

CROSS-REFERENCE TO RELATED APPLICATIONS

This application is the National Stage entry under § 371 of International Application No. PCT/EP2020/076853, filed on Sep. 25, 2020, and which claims the benefit of priority to European Application No. 19200713.6, filed on Oct. 1, 2019. The content of each of these applications is hereby incorporated by reference in its entirely,

BACKGROUND OF THE INVENTION

Field of the Invention

The invention is in the field of processes for preparing nanoparticles, comprising at least one bio-resorbable polyester, in the form of a powder, by emulsion-solvent extraction or emulsion-solvent evaporation and application of ultrasonic sound.

Description of Related Art Background

WO2004/026452A1 describes a method and flow-through cell for continuous treatment of free-flowing compositions by means of ultrasound. The method employs an ultrasonic sound flow-through cell, comprising a cylindrical glass tube through which an emulsion fluid may be transported. The cylindrical glass tube is inserted into a steel mantle, wherein an open space is filled with pressured water in the range of 2 to 20 bar as ultrasonic transducer. The ultrasonic transducer is excited by a high frequency generator (sonotrode) for the transmission of the sound waves indirectly via the ultrasonic transducer to a through passing fluid. In example 1, 5% by weight of a poly(lactide-co-glycolide) (PLGA) in dichloromethane (DCM) and a solution of 10% by weight bovine serum albumin (BSA) in aqueous phosphate buffer are combined to a joint stream and passed through a flow-through cell with a glass tube of 50 cm in length and 2 mm inner diameter under ultrasonic sound. A water-in-oil emulsion is generated with a mean diameter of the droplets from 0.62 to 1.37 µm. It is mentioned that the emulsions were stable for >30 min and would therefore be in general suitable for further processing to microspheres. The high frequency generator has a 100% power output of 30 to 35, preferably of 32 W. WO2004/026452A1 uses an ultrasonic sound flow-through cell, comprising a cylindrical glass tube with a sonication zone with a power input of the ultrasound transducer of calculated 51.4 W per $cm^3$ of the joint stream of dispersed and continuous phase.

WO2015/181138A1 describes multi layered calcium phosphate nanoparticles with a diameter in the range of 10 to 300 nm and a process for preparing the nanoparticles. For the formation of water-in-oil and water-in-oil-in-water emulsions, sonication (ultrasonic) was carried out with a Hielscher UP50H instrument, sonotrode MS2, 70% amplitude, pulse 0.7, for 20 s.

Freitas S. et al. (European Journal of Pharmaceutics and Biopharmaceutics 61 (2005) 181-187) describes flow-through ultrasonic emulsification combined with static micromixing for aseptic production of microspheres by solvent extraction. PLGA (RESOMER® RG 503 H) particles were prepared from water-in-oil-in-water emulsions ($W_1/O/W_2$) in a solvent extraction/evaporation process. The particle sizes of the droplets in the primary emulsion ($W_1/O$) were 0.63+/−0.03 µm and the particle sizes in the double emulsion ($W_1/O/W_2$) 14.8 µm or higher. Freitas used an ultrasonic sound flow-through cell (Dmini250, Dr. Hielscher, Teltow, Germany) comprising a cylindrical glass tube with a sonication zone with a calculated power input of the ultrasound transducer of calculated 48.2 W per $cm^3$ of the joint stream of dispersed and continuous phase.

Freitas S. et al. (Ultrasonics Sonochemistry 13 (2006) 76-85) describes continuous contact- and contamination-free ultrasonic emulsification—a useful tool for pharmaceutical development and production. PLGA (RESOMER® RG 503 H) particles were prepared from oil-in-water emulsions (O/W) in a solvent extraction/evaporation process. PLGA mean particle sizes prepared under different conditions ranged from 0.49 to 0.60+/−0.02 µm. Freitas used an ultrasonic sound flow-through cell, comprising a cylindrical glass tube (2 mm inner diameter) with a sonication zone with a power input of the sonotrode (24 kHz, UIP250, Dr. Hielscher) of calculated 51.4 W per $cm^3$ of the joint stream of dispersed and continuous phase.

Dördelmann G. (Dissertation (2015) University Duisburg, Faculty of Chemistry, Essen, Germany) describes calcium phosphate nanoparticles combined with bio-degradable polymers as composite materials for active ingredient transport and bone substitution material. Dördelmann uses an ultrasonic sound flow-through cell, comprising a cylindrical glass tube with a sonication zone with a power input of the sonotrode of calculated 51.4 W per $cm^3$ of the joint stream of dispersed and continuous phase. Dördelmann uses the ultrasonic device for homogenization of a pre-emulsion W/O of calcium phosphate nanoparticles in an aqueous suspension and bio-degradable polymers in an organic solution. The dispersed phase did not contain a biodegradable polymeric material. Homogenized nanodroplets of aqueous suspension of calcium phosphate in an organic PLGA solution were collected and nanoparticles were prepared subsequently via rapid precipitation in an ethanol phase. The max. flowrate was 3.3 ml/min and a maximum of 50 mg/min of resulting nanoparticles is described.

SUMMARY OF THE INVENTION

There is a technical need for processes to provide nanoparticles, comprising bio-resorbable polyesters, in in the form of fine powders. The invention is therefore concerned with a process for preparing nanoparticles, comprising a bio-resorbable polyester, in the form of a powder with a Z-Average particle size $D_z$ in the range of 1 to 450 nm, preferably 10 to 300 nm, most preferably 50 to 200 nm, with a polydispersity index (PDI) in the range of 0.01 to 0.5, preferably 0.01 to 0.4, most preferably 0.05 to 0.38, from a bio-resorbable polyester by emulsion-solvent extraction or emulsion-solvent evaporation and application of ultrasonic sound as described herein. The inventors have found that one of the key factors of their invention to gain the comparatively small sized nanoparticles is the passing of the joint stream of a dispersed polymer phase and a continuous phase through an ultrasonic sound flow-through cell under sonication with a power input of 20 to 50, preferably 27 to 45 W per $cm^3$ joint stream. In contrast to the present findings one would have rather expected from the teaching of Freitas et al. (2006), where a power input of calculated 51.4 W/$cm^3$ had been used, that a lower power input would lead to larger particles of 500 nm diameter or more. Surprisingly, smaller bio-resorbable polyester particles, optionally com-

DETAILED DESCRIPTION OF THE INVENTION

The invention is concerned with a process for preparing nanoparticles, comprising at least one bio-resorbable polyester, in the form of a powder with a Z-Average particle size $D_z$ in the range of 1 to 450 nm, preferably 10 to 300 nm, most preferably 50 to 200 nm, with a polydispersity index PDI in the range of 0.01 to 0.5, preferably 0.01 to 0.4, most preferably 0.05 to 0.38, by emulsion-solvent extraction or emulsion-solvent evaporation and application of ultrasonic sound comprising the steps a) to f):

a) providing an organic phase (OP), comprising a solvent or solvent mixture S1, comprising one or more organic solvent(s), comprising 0.1 to 55, preferably 0.4 to 50% by weight of the bio-resorbable polyester, in a first container.

The first container may be for instance a beaker, a feed vessel or a holding tank.

b) providing an aqueous phase (AP), comprising a solvent or solvent mixture S2, comprising water and an emulsion stabilizing agent, in a second container.

The second container may be for instance a beaker, a feed vessel or a holding tank.

c) providing streams of the organic phase (OP) and of the aqueous phase (AP) and joining the streams to a joint stream.

The separate streams of the organic phase (OP) from the first container and of the aqueous phase (AP) from the second container may be usually provided through hoses or tubes driven for instance by means of pumping devices. The application of other driving forces like simple gravity, pressure or vacuum is also possible. The separate streams may then be joined before or in the entrance zone of the ultrasonic sound flow-through cell. The separate streams may be joined for instance by means of a common tube connection (T- or Y-connection) or for instance in a pre-mixing device cell in which the streams are joined and optionally pre-mixed.

d) passing the joint stream through an ultrasonic sound flow-through cell under sonication with a power input of 20 to 50, preferably 27 to 45 W per cm³ joint stream, to result in an emulsion appearing at the outlet of the ultrasonic sound flow-through cell.

The power input in W per cm³ joint stream is calculated as follows:

$$\text{Power Input} = \frac{P}{Vs} = \frac{4P}{ID^2 \pi * l}$$

P being the power generated in the instrument

Vs being the volume within the sonication field (which is calculated from the inner diameter (ID) and the length (l) of the sonication zone of the tube)

e) removal of the solvents or solvent mixture(s) S1 and S2 by evaporation or by mixing the emulsion with an excess amount of an aqueous extraction phase (EP) to form a combined phase resulting in the removal of the solvent or solvent mixture S1 from the emulsion and in the formation of nanoparticles of the bio-resorbable polyester, f) obtaining the nanoparticles comprising the bio-resorbable polyester from the evaporated or from the combined extraction phase by concentration and drying to obtain a polymer powder with a Z-Average particle size $D_z$ in the range of 1 to 450 nm, preferably 10 to 300 nm, most preferably 50 to 200 nm, with a PDI value in the range of 0.01 to 0.5, preferably 0.01 to 0.4, most preferably 0.05 to 0.38.

Bio-Resorbable Polyester

In step a) an organic phase (OP), comprising a solvent or solvent mixture S1, comprising 0.1 to 55, preferably 0.4 to 50, most preferably 0.5 to 25% by weight of the bio-resorbable polyester, is provided.

The term "bio-resorbable" in "bio-resorbable polyester" means that such a polyester, which is preferably a lactic acid or lactide-based polymer and which is after implantation or injection in the human body or in the body of an animal in contact with the body fluids, is broken down into oligomers in a slow hydrolytic reaction. Hydrolysis end-products such as lactic acid or glycolic acid are metabolized into carbon dioxide and water. Other exchangeable expressions for the term "bio-resorbable polyester" which are often used are "resorbable polyester", "reabsorbable polyester", "bio-degradable polyester" or "adsorptive polyester".

The bio-resorbable polyester may be selected from polyorthoesters, polylactides, polydioxanones, polycaprolactones, polytrimethyl carbonates, polyglycolides, poly(lactide-co-glycolide) (PLGA), poly(lactide-co-caprolactone), poly(lactide-co-trimethyl carbonate), poly(lactide-co-polyethylene-glycol) and any blends thereof. Preferably the bio-resorbable polyester is selected from polyorthoesters, poly(lactide-co-glycolide) (PLGA) or blends thereof.

Active Pharmaceutical Ingredient

The organic phase (OP) or the aqueous phase (AP) or both may comprise an active pharmaceutical ingredient.

The active pharmaceutical ingredient may be selected from the groups of analgesics, antibiotics or anti-infectives, antibodies, antiepileptics, antigens from plants, antirheumatics, benzimidazole derivatives, beta-blockers, cardiovascular drugs, chemotherapeutics, CNS drugs, digitalis glycosides, gastrointestinal drugs, e.g. proton pump inhibitors, combinations of proton pump inhibitors with a nonsteroidal anti-inflammatory drug (NSAID), enzymes, hormones, liquid or solid natural extracts, oligonucleotides, DNA, RNA, mRNA, siRNA, Protacs (proteolysis targeting chimera), peptide hormones, therapeutic bacteria, peptides, proteins, urology drugs and vaccines, including salt-forms, such as aspartates or hydrochlorides. Suitable are for instance diclofenac or ritonavir including their salt-forms (for instance diclofenac sodium).

Ultrasonic Sound Flow-Through Cell

The ultrasonic sound flow-through cell comprises a cylindrical glass tube with a sonication zone through which the emulsion fluid is transported, which is inserted into a steel mantle, wherein there is an open space between the glass tube and the steel mantle, wherein the open space is filled with a pressured liquid, preferably water, of 5 to 15, preferably 8 to 12 bar as ultrasonic transducer, wherein the ultrasonic transducer is excited by an attached 18 to 22 kHz, preferably a 20 kHz high-frequency generator (sonotrode) for transmission of the sound waves, wherein the high frequency generator has a power output of 1 to 200 W, preferably of 80 to 110 W.

The section of the cylindrical glass tube in which the joint stream of organic phase (OP) and aqueous phase (AP) is treated with ultrasound from the sonotrode through the glass mantle and the ultrasonic transducer in d) is called sonication zone. The cylindrical glass tube is usually longer than the sonication zone.

The sonication zone of the cylindrical glass tube may have a length of 150 to 250, preferably 180 to 220 mm and an inner diameter of 2.0 to 6.5, preferably 3.5 to 5.5 mm. The thickness of the glass wall may be 0.5 to 2 mm, preferably 0.8 to 1.5 mm.

The cylindrical tube can also be made from rigid plastic, metal or any other materials able to transfer energy.

The residence time of the joint stream in the sonication zone of the ultrasonic sound flow-through cell may be from 0.5 to 80, preferably from 2 to 50 seconds.

The flow rate of the joint stream in the ultrasonic sound flow-through cell may be from 2 to 200, preferably 4 to 40 ml/min.

Oil-In-Water (O/W) Emulsion

In d), an (a final) oil-in-water (O/W) emulsion may be formed.

In this case, in step c) the streams of the organic phase (OP) and the aqueous phase (AP) may be provided at flow rates of 0.5 to 50, preferably 1 to 10 ml/min of the organic phase (OP) and 1.5 to 150, preferably 3 to 30 ml/min of the aqueous phase (AP), with the proviso that the flow rate of the aqueous phase (AP) should be higher than that of the organic phase (OP), resulting in an oil-in-water emulsion (O/W) in d).

In the case of the oil-in-water (O/W) emulsion, the organic phase (OP) is a dispersed phase and the aqueous phase (AP) is a continuous phase.

Water-In-Oil-In-Water Emulsion ($W_1/O/W_2$)

Alternatively, in step d), a primary (intermediate) water-in-oil ($W_1/O$) emulsion may be formed, which is then, before step e), mixed and emulsified with an additional water phase ($W_2$), preferably by means of a static mixer or a further sonication flow-through cell, to give a final water-in-oil-in-water emulsion ($W_1/O/W_2$). The water phase $W_2$ is usually added in excess volume to the water-in-oil ($W_1/O$) emulsion.

In this case, in step c) the streams of the organic phase (OP) and the aqueous phase (AP) may be provided at flow rates of 1.5 to 150, preferably 3 to 30 ml/min of the organic phase (OP) and 0.5 to 50, preferably 1 to 10 ml/min of the aqueous phase (AP), with the proviso that the flow rate of the organic phase (OP) is higher than that of the aqueous phase (AP), resulting in the primary water-in-oil emulsion ($W_1/O$) in d). If a further sonication flow-through cell is used to create the ($W_1/O/W_2$) emulsion, the flow rate of the water phase ($W_2$) should be higher than the joint flow rate of the ($W_1/O$) emulsion.

In the case of the primary (intermediate) water-in-oil ($W_1/O$) emulsion, the organic phase (OP) is a continuous phase and the aqueous phase (AP) is a dispersed phase.

Organic Phase (OP)

In step a) an organic phase (OP), comprising a solvent or solvent mixture S1, comprising one or more organic solvent(s) is provided. The organic phase further comprises 0.1 to 55, preferably 0.4 to 50% by weight of a bioresorbable polyester, is provided in a first container.

The organic phase (OP) may comprise a solvent or solvent mixture S1, which is not or only partially miscible with the solvent or solvent mixture of the aqueous phase (AP).

The term "not miscible" shall mean that separate phases (OP) and (AP) are formed at any mixing ratios, for instance at 25° C.

The term "partially miscible" shall mean that a part, usually less than 25% or less than 10% by weight, for instance at 25° C., of the solvent or solvent mixture S1 can dissociate or move into the solvent or solvent mixture S2 of the aqueous phase (AP).

The solvent or solvent mixture S1 may comprise one or more organic solvent(s), for example, selected from dichloromethane (DCM), ethyl acetate (EtOAc), chloroform, benzyl alcohol, diethyl carbonate (DMC), dimethyl sulfoxide (DMSO), methanol, propylene carbonate, isopropyl acetate, methyl acetate, methyl ethyl ketone, butyl lactate and isovaleric acid or any mixture thereof. A preferred solvent or solvent mixture S1 may comprise EtOAc, DCM, EtOAc and DMSO or DCM and DMSO.

For instance, when the aqueous phase (AP) may be water or may contain from 90% by weight and up to 100% water as solvent S2, a suitable solvent mixture S1 may be selected from dichloromethane (DCM), ethyl acetate (EtOAc) or dimethyl sulfoxide (DMSO) and methanol, for instance at a ratio from 1:9 to 9:1).

For instance, when the aqueous phase (AP) may be water or may contain from 90% by weight and up to 100% water as solvent S2, a suitable solvent mixture S1 may be mixture of ethyl acetate (EtOAc) and dimethyl sulfoxide (DMSO), for instance at a ratio from 1:9 to 9:1.

For instance, when the aqueous phase (AP) may be water or may contain from 90% by weight and up to 100% water as solvent S2, another suitable solvent mixture S1 may be a mixture of dichloromethane (DCM) and dimethyl sulfoxide (DMSO), for instance at a ratio from 1:9 to 9:1.

The organic phase (OP) may comprise an active pharmaceutical ingredient. The organic phase (OP) may comprise up to 25, preferably 0.1 to 15% by weight of an active pharmaceutical ingredient.

Aqueous Phase (AP)

The aqueous phase (AP) comprises a solvent or solvent mixture S2, comprising water, preferably 75% by weight or more. The solvent or solvent mixture S2 is not or only partially miscible with the (organic) solvent or the solvent mixture S1 so that the aqueous phase (AP) and the organic phase (OP) form separate phases after mixing, preferably at any ratios from 1:9 to 9:1 and between about 5 and 35° C., preferably from 20 to 25° C.

The term "not miscible" shall mean that separate phases (OP) and (AP) are formed at any mixing ratios, for instance at 25° C.

The term "partially miscible" shall mean that a part, usually less than 25% or less than 10% by weight, for instance at 25° C., of the solvent or solvent mixture S1 can dissociate or move into the solvent or solvent mixture S2 of the aqueous phase (AP).

To give an example: If the solvent S1 of the organic phase (OP) is for instance ethyl acetate and the solvent S2 of the aqueous phase (AP) is water, a small amount of ethyl acetate, about up to 8% by weight, may dissociate or move after mixing into the aqueous water phase (AP). However, the remaining mixed phases are still separate and can be processed as disclosed herein. If such a movement of partially water miscible organic solvent S1 into the aqueous phase (AP) shall be avoided, the solvent S2, water, of the aqueous phase (AP) may be saturated from the beginning by addition of the corresponding organic solvent, in this example with about 8% by weight ethyl acetate, before contacting with the organic phase (OP).

The aqueous phase (AP) is comprising a solvent or solvent mixture S2.

The solvent or solvent mixture S2 may comprise 60% or more and up to 100%, preferably 80% or more and up to 100% by weight of water.

The aqueous phase (AP) comprises a solvent or solvent mixture S2, comprising water, which is not or only partially miscible with the solvent or the solvent mixture S1 of the organic phase (OP) so that the aqueous phase (AP) and the organic phase (OP) form separate phases after mixing. The separate phases can be processed as disclosed herein.

The solvent or solvent mixture S2 may comprise water and optionally a solvent fully miscible with water and not or only partially soluble in the solvent or solvent mixture S1.

The solvent or solvent mixture S2 may comprise at least 60% by weight (60% by weight or more), preferably at least 80% (80% by weight or more) by weight of water and optionally up to 40% by weight, preferably up to 20% by weight of, for example, ethanol, acetone, isopropanol, dichloromethane (DCM), ethyl acetate (EtOAc), chloroform, benzyl alcohol, diethyl carbonate (DMC), dimethyl sulfoxide (DMSO), methanol, propylene carbonate, isopropyl acetate, methyl acetate, methyl ethyl ketone, butyl lactate, isovaleric acid or any mixtures thereof.

The aqueous phase (AP) may comprise water and an emulsion stabilizing agent. The aqueous phase (AP) may comprise water and 0.1 to 10, preferably 1 to 8% by weight of an emulsion stabilizing agent, preferably polyvinyl alcohol (PVA) or polysorbate.

The aqueous phase (AP) may optionally comprise an active pharmaceutical ingredient. The aqueous phase (AP) may comprise up to 25, preferably 0.1 to 15% by weight of an active pharmaceutical ingredient.

Emulsion-Solvent Extraction/Aqueous Extraction Phase (EP)

The nanoparticles may be obtained in step e) from the emulsion by emulsion-solvent-extraction.

The aqueous extraction phase (EP) may comprise from 80% or more, at least 80 and up to 100% by weight of water.

The aqueous extraction phase (EP) may comprise at least 80% by weight of water and optionally up to 20% water-miscible solvents, for instance ethanol, acetone, isopropanol or any mixtures thereof. The extraction phase (EP) may further comprise 0 to 10, preferably 1 to 8% by weight of an emulsion stabilizing agent, such as polyvinyl alcohol (PVA) or polysorbate.

In step e) the emulsion may be mixed with an excess amount of the aqueous extraction phase (EP) to form a combined phase resulting in the removal of the solvent S1 from the emulsion and in the formation of nanoparticles of the bio-resorbable polyester or of a mixture of an active pharmaceutical ingredient and the bio-resorbable polyester. An excess amount of an aqueous extraction phase is 2 to 150 times, preferably 5 to 70 times of the volume of the emulsion.

Emulsion-Solvent Evaporation

The nanoparticles may be obtained in step e) from the emulsion by emulsion-solvent evaporation. The process of emulsion-solvent evaporation is well known to a skilled person in the field. The solvents S1 and/or S2 may be removed by evaporation which results in the formation of nanoparticles of the bio-resorbable polyester or of a mixture of an active pharmaceutical ingredient and the bio-resorbable polyester.

Nanoparticles

The nanoparticles obtained by the process as disclosed show a homogeneous surface structure. The homogeneous structure can be shown for instance by electron microscopic imaging.

Polymer Powder: Z-Average Size $D_z$ and PDI

The polymer powder, comprising the bio-resorbable polyester and optionally an active pharmaceutical ingredient, has a Z-Average size $D_z$ (Z-Average particle size $D_z$) in the range of 1 to 450 nm, preferably 10 to 300 nm, more preferably 50 to 200 nm, with a PDI value in the range of 0.01 to 0.5, preferably 0.01 to 0.4, more preferably 0.05 to 0.38. The Z-Average size $D_z$ may be determined by dynamic light scattering (DLS) according to ISO 22412:2017 (publication date 2017-02) "Particle size analysis—Dynamic light scattering (DLS)".

Dynamic light scattering (DLS), also known as photon correlation spectroscopy (PCS) or quasielastic light scattering (QELS) is the widely available method employed for routine analysis of hydrodynamic size of the particles in solution. This method relies upon the measurement of scattering intensity of nanoparticles in Brownian motion when illuminated by a monochromatic beam of light. This scattering intensity fluctuates on a microsecond timescale, the fluctuations corresponding to the diffusion rate of the particles.

The polydispersity index (PDI) is determined from a two-parameter fit to the correlation data (the cumulants analysis). The calculations used for the determination of PDI are defined in the ISO standard documents 22412:2017.

Items

The invention may be summarized by the following Items:

1. A process for preparing nanoparticles, comprising at least one bio-resorbable polyester, in the form of a powder with a Z-Average particle size $D_z$ in the range of 1 to 450 nm, with a polydispersity index PDI in the range of 0.01 to 0.5, by emulsion-solvent extraction or emulsion-solvent evaporation and application of ultrasonic sound comprising the steps a) to f):
    a) providing an organic phase (OP), comprising a solvent or solvent mixture S1, comprising one or more organic solvents, comprising 0.1 to 55% by weight of the bio-resorbable polyester, in a first container,
    b) providing an aqueous phase (AP), comprising a solvent or solvent mixture S2, comprising water, and an emulsion stabilizing agent, in a second container,
    c) providing streams of the organic phase (OP) and the aqueous phase (AP) and joining the streams to a joint stream,
    d) passing the joint stream through an ultrasonic sound flow-through cell under sonication with a power input of 20 to 50 W per $cm^3$ joint stream, to result in an emulsion appearing at the outlet of the ultrasonic sound flow-through cell,
    e) removal of the solvents or solvent mixture(s) S1 and S2 by evaporation or by mixing the emulsion with an excess amount of an aqueous extraction phase (EP) to form a combined phase, resulting in the removal of the solvent or solvent mixture S1 from the emulsion and in the formation of nanoparticles,
    f) obtaining the nanoparticles comprising the bio-resorbable polyester from the evaporated or from the combined extraction phase by concentration and drying to obtain a polymer powder with a Z-Average particle size $D_z$ in the range of 1 to 450 nm and with a polydispersity index PDI in the range of 0.01 to 0.5.

2. Process according to Item 1, wherein the organic phase (OP) comprises a solvent or solvent mixture S1, which is not or only partially miscible with the solvent or solvent mixture of the aqueous phase (AP).
3. Process according to Item 1 or 2, wherein in d) an oil-in-water (O/W) emulsion is formed.
4. Process according to Item 1 or 2, wherein in d) a water-in-oil ($W_1$/O) emulsion is formed, which is, before e), mixed and emulsified with an additional water phase ($W_2$), preferably by means of a static mixer or a further sonication flow-through cell, to give a water-in-oil-in-water emulsion ($W_1$/O/$W_2$).
5. Process according to any one of Items 1 to 4, wherein the solvent or solvent mixture S1 comprises dichloromethane, ethyl acetate, chloroform, benzyl alcohol, diethyl carbonate, dimethyl sulfoxide, methanol, propylene carbonate, isopropyl acetate, methyl acetate, methyl ethyl ketone, butyl lactate, isovaleric acid or any mixture thereof.
6. Process according to any one of Items 1 to 5, wherein the solvent or solvent mixture S2 comprises 60 or more and up to 100% by weight of water.
7. Process according to Item 6 wherein the solvent or the solvent mixture S2, wherein the solvent or the solvent mixture S2 is not or only partially miscible with the (organic) solvent or the solvent mixture S1 so that the aqueous phase (AP) and the organic phase (OP) form separate phases after mixing.
8. Process according to any one of Items 1 to 7, wherein the aqueous phase (AP) 0.1 to 10% by weight of an emulsion stabilizing agent, preferably polyvinyl alcohol or polysorbate.
9. Process according to any one of Items 1 to 8, wherein the aqueous extraction phase (EP) comprises 80% or more by weight of water.
10. Process according to any one of Items 1 to 9, wherein the bio-resorbable polyester is selected from polyorthoesters, polylactides, polydioxanones, polycaprolactones, polytrimethyl carbonates, polyglycolides, poly(lactide-co-glycolide), poly(lactide-co-caprolactone), poly(lactide-co-trimethyl carbonate), poly(lactide-co-polyethylene-glycol) and any blends thereof.
11. Process according to any one of Items 1 to 9, wherein the organic phase (OP) comprises an active pharmaceutical ingredient.
12. Process according to any one of Items 1 to 9, wherein the aqueous phase (AP) comprise(s) an active pharmaceutical ingredient.
13. Process according to any one of Items 1 to 3 and 5 to 12, wherein in c) the streams of the organic phase (OP) and the aqueous phase (AP) are provided at flow rates of 0.5 to 50 ml/min of the organic phase (OP) and 1.5 to 150 ml/min of the aqueous phase (AP), with the proviso that the flow rate of the aqueous phase (AP) is higher than that of the organic phase (OP), resulting in an oil-in-water emulsion (O/W) in d).
14. Process according to any one of Items 1 to 2 and 4 to 12, wherein in c) the streams of the organic phase (OP) and the aqueous phase (AP) are provided at flow rates of 1.5 to 150 ml/min of the organic phase (OP) and 0.5 to 50 ml/min of the aqueous phase (AP), with the proviso that the flow rate of the organic phase (OP) is higher than that of the aqueous phase (AP), resulting in a water-in-oil emulsion ($W_1$/O) in d).
15. Process according to any one of Items 1 to 14, wherein the residence time of the joint stream in the ultrasonic sound flow-through cell is from 0.5 to 80 seconds.
16. Process according to any one of Items 1 to 15, wherein the flow rate of the joint stream in the ultrasonic sound flow-through cell is from 2 to 200 ml/min.
17. Process according to any one of Items 1 to 16, wherein the ultrasonic sound flow-through cell comprises a cylindrical glass, metal, or rigid plastic tube with a sonication zone through which the emulsion fluid is transported, which is inserted into a steel mantle, wherein there is an open space between the tube and the steel mantle, wherein the open space is filled with a pressured liquid, preferably water, of 5 to 15 bar as ultrasonic transducer, wherein the ultrasonic transducer is excited by an attached 18 to 22 kHz, preferably a 20 kHz high-frequency generator (sonotrode) for transmission of the sound waves, wherein the high-frequency generator has a 10-100%, preferably 60-100%, most preferably 80-100% amplitude and a power output range from 1 to 200 W, preferably 80 to 110 W.
18. Process according to any one of Items 1 to 17, wherein the sonication zone of the cylindrical tube has a length of 150 to 250, preferably 180 to 220 mm and an inner diameter of 2.0 to 6.5, preferably 3.5 to 5.5 mm.
19. Process according to any one of Items 1 to 18, wherein the solvent or solvent mixture S2 comprises at least 60% by weight, preferably at least 80% by weight of water and optionally up to 40% by weight, preferably up to 20% by weight of ethanol, acetone, isopropanol, dichloromethane (DCM), ethyl acetate (EtOAc), chloroform, benzyl alcohol, diethyl carbonate (DMC), dimethyl sulfoxide (DMSO), methanol, propylene carbonate, isopropyl acetate, methyl acetate, methyl ethyl ketone, butyl lactate, isovaleric acid or any mixtures thereof.
20. Process according to any one of Items 1 to 19, wherein the organic phase (OP) comprises up to 25, preferably 0.1 to 15% by weight of an active pharmaceutical ingredient.
21. Process according to any one of Items 1 to 20, wherein the aqueous phase (AP) comprises up to 25, preferably 0.1 to 15% by weight of an active pharmaceutical ingredient.

EXAMPLES

Materials

For Examples 1 to 3

PLGA=Poly(D,L-lactide-co-glycolide) 50:50 (RESOMER® RG 502 H, $M_w$=7,000-17,000 g mol$^{-1}$, Evonik Industries AG (Darmstadt)). Polyvinyl alcohol (PVA, $M_w$=~31,000 g mol$^{-1}$, 86-90% hydrolyzed) was purchased from Sigma-Aldrich. Ethyl acetate and Dichloromethane (both J. T. Baker—Avantor® Performance Materials, LLC) were either used as solvents for the polymer. For encapsulation experiments ritonavir ($M_w$=720.95, Angene international limited) and diclofenac sodium (Sigma Aldrich), respectively, was used and dissolved first in dimethyl sulfoxide (DMSO, WAK-Chemie Medical GmbH).

For Examples 4 to 7

The polymer film was composed of 70 wt % polyorthoester (POE) and 30 wt % RESOMER® Select 7525 DLG 8E ((PLGA)=(Poly(D,L-lactide-co-glycolide) obtained from 75 mole-% DL-lactide and 25 mole-% glycolide), Evonik Industries AG (Darmstadt). RESOMER® Select 7525 DLG 8E, Evonik Industries AG (Darmstadt) was additionally employed as single substance. Polyvinyl alcohol (PVA, Mw=~31,000 g mol-1, 86-90% hydrolyzed, Sigma-Aldrich), ethyl acetate (J. T. Baker—Avantor® Performance Materials, LLC) and MilliQ water were used as solvents.

All other chemicals were of analytical grade and used without further purification.

Instruments

For the formation of oil-in-water, water-in-oil and water-in-oil-in-water emulsions, sonication (ultrasonic) was carried out in GDmini2 (Hielscher Ultrasonics GmbH). A cylindrical glass tube with a length of 198 mm and an inner diameter of 4.00 mm was utilized. The thickness of the glass wall was 1 mm. Dynamic light scattering was applied for determination of particle size using a Zetasizer nanoseries instrument (Malvern Nano-ZS, laser: λ=532 nm). The data was taken from the Malvern software without further correction.

The particle size data refer to scattering intensity distributions (z-average). Diafiltration was performed at ambient temperature with a KrosFlo® Kr2i and a 750 kD modified polyether sulfone filtration module (Spectrum labs) in examples 1 to 3.

Drug load and encapsulation efficiencies were determined by HPLC.

Calculation for encapsulation efficiency and drug load:

$$\text{Encapsulation efficiecny} = \frac{\text{amount of drug encapsulated in particles [mg]}}{\text{total amount of drug used [mg]}} * 100[\%]$$

$$\text{Drug load} = \frac{\text{amount of drug encapsulated in particles [mg]}}{\text{weight of dry nanoparticle formulation [mg]}} * 100[\%]$$

Example 1: Synthesis of PLGA-ritonavir nanoparticles
Example 2: Synthesis of PLGA-diclofenac sodium nanoparticles
Example 3: Synthesis of PLGA nanoparticles
Example 4: Synthesis of 6% POE-PLGA nanoparticles
Example 5: Synthesis of 15% POE-PLGA nanoparticles
Example 6: Synthesis of 30% POE-PLGA nanoparticles
Example 7: Synthesis of 50% POE-PLGA nanoparticles Example 1: Synthesis of PLGA-Ritonavir Nanoparticles For the synthesis of particles containing ritonavir, a water insoluble active ingredient, an O/W-emulsion was prepared. For this, two solutions (A and B) were constantly fed to an indirect sonication device. The aqueous Solution A containing the stabilizer PVA was emulsified with the organic Solution B containing the polymer and the active ingredient by sonication. The emulsion was combined with an additional aqueous extraction phase, continuously added after the emulsification to extract the solvent.

This led to solid polymeric nanoparticles as the partially water miscible solvent was extracted into the excessive amount of water. Thereby an almost transparent white milky dispersion was created. 1.8 g PLGA were dissolved in ethyl acetate (PLGA: 225.5 mg mL$^{-1}$; 7.98 mL) and 0.2 g ritonavir were dissolved in dimethyl sulfoxide (DMSO) (ritonavir: 57.9 mg mL$^{-1}$, 3.45 mL). Both phases were combined and mixed to result in Solution B, the dispersed phase (=organic phase (OP)). This phase was joined with solution A (=aqueous phase (AP)), the aqueous phase containing polyvinyl alcohol (PVA; 20 mg mL$^{-1}$; 34.31 mL), directly in front of the sonication device using a T-junction at a flow rate of 8 mL/min and 24 mL/min respectively. This mixture was then continuously pumped into the sonication device and emulsified to form a white, milky O/W-emulsion. The time of exposure to the sonication field was 4.7 seconds at an amplitude of 100%, a temperature of 14° C. and a pressure of 9 bar within the transmitting fluid. Directly after the sonication device, deionized water (=aqueous extraction phase (EP)) was introduced to the emulsion through a second T-junction at a flow rate of 162 mL/min and diluted the emulsion. During this step, ethyl acetate was extracted, the PLGA particles solidified and ritonavir was incorporated into the PLGA matrix.

Tangential flow filtration was used to remove the excess of PVA, ethyl acetate, DMSO and free ritonavir as well as concentrate the particle suspension. The concentrated nanoparticle suspension was then freeze-dried with addition of 3% trehalose as cryoprotectant. The particles were easily re-dispersible in water by gentle shaking.

To determine the encapsulation efficiency of ritonavir, the particles were dissolved in acetonitrile and analyzed by HPLC after previous calibration with dissolved ritonavir.

The ritonavir-PLGA nanoparticles contained 53.0 mg/g ritonavir which corresponds to an encapsulation efficiency of 53.0%.

| Particle size D$_z$ [nm] | PDI | Power Input [W/cm$^3$] |
| --- | --- | --- |
| 175.53 | 0.147 | 34.0 |

Example 2: Synthesis of PLGA-Diclofenac Sodium Nanoparticles

An O/W-emulsion was prepared in a first step. For this, two solutions (A and B) were constantly fed to an indirect sonication device. The aqueous Solution A containing the stabilizer PVA was emulsified with the organic Solution B containing the polymer and the active ingredient by sonication. The emulsion was combined with an additional aqueous extraction phase, continuously added after the emulsification to extract the solvent.

This led to solid polymeric nanoparticles as the partially water miscible solvent was extracted into the excessive amount of water. Thereby an almost transparent white milky dispersion was created.

To prepare solution A, 0.3 g polyvinyl alcohol (PVA) was dissolved in 30 mL deionized water. The dispersed phase, Solution B, contained 1.67 g PLGA in ethyl acetate (225.5 mg mL$^{-1}$, 7.39 mL) and 0.33 g diclofenac in DMSO (400.1 mg mL$^{-1}$, 1.21 mL). Solution A and Solution B were continuously combined in a T-junction directly in front of the sonication device in a ratio of 3:1 at a flow rate of 2 mL/min and 6 mL/min. The mixture was then emulsified within the sonication device cooled to 14° C. at 100% amplitude to form a white, milky O/W-emulsion. The pressure of the transmitting fluid was 9 bar and the residence time of the mixture within the sonication field was 18.7 seconds. Directly after the sonication device deionized water was introduced to the emulsion through a second T-junction at a flow rate of 52 mL/min and diluted the emulsion. During this step, ethyl acetate was extracted, the PLGA particles solidified and diclofenac sodium was incorporated into the PLGA matrix.

Tangential flow filtration was used to remove the excess of PVA, ethyl acetate, DMSO and free diclofenac sodium as well as concentrate the particle suspension. The concentrated nanoparticle suspension was then freeze-dried with addition of 3% trehalose as cryoprotectant. The particles were re-dispersed in water using vortex for 1 minute.

| Particle size $D_z$ [nm] | PDI | Power Input [W/cm$^3$] |
|---|---|---|
| 74.96 | 0.35 | 37.6 |

Example 3: Synthesis of PLGA Nanoparticles

For the synthesis of placebo particles, two solutions (A and B) were constantly fed to the indirect sonication device. The aqueous Solution A containing the stabilizer PVA was emulsified with the organic Solution B containing the polymer by sonication. The emulsion was combined with an additional aqueous extraction phase, continuously added after the emulsification in order to extract the solvent.

This led to solid polymeric nanoparticles as the partially water miscible solvent was extracted into the excessive amount of water. Thereby an almost transparent white milky dispersion was created. 2 g PLGA were dissolved in ethyl acetate (PLGA: 200 mg mL$^{-1}$; 4 mL) to result in Solution B, the dispersed phase. This phase was joined with solution A, the aqueous phase containing polyvinyl alcohol (PVA; 20 mg mL$^{-1}$; 12 mL) directly in front of the sonication device using a T-junction at a flow rate of 2 mL/min and 6 mL/min, 5 mL/min and 15 mL/min, 8 mL/min and 24 mL/min, respectively. This mixture was then continuously pumped into the sonication device and emulsified to form a white, milky O/W-emulsion. The time of exposure to the sonication field was 18.7 seconds, 7.5 seconds or 4.7 seconds, respectively at an amplitude of 100%, a temperature of 14° C. and a pressure of 9 bar within the transmitting fluid. Directly after the sonication device, deionized water was introduced to the emulsion through a second T-junction at a flow rate of 63 mL/min, 121 mL/min and 193 mL/min respectively, and diluted the emulsion. During this, ethyl acetate was extracted, the PLGA particle solidified.

| Flow rate of solution A [mL/min] | Flow rate of solution B [mL/min] | Particle size $D_z$ [nm] | PDI | Power Input [W/cm$^3$] |
|---|---|---|---|---|
| 6 | 2 | 151.93 | 0.099 | 42.4 |
| 15 | 5 | 148.17 | 0.086 | 42.4 |
| 24 | 8 | 155.30 | 0.097 | 42.4 |

Examples 4 to 7

For the synthesis of POE-PLGA particles, an O/W-emulsion was prepared. Four different percentages of POE/PLGA have been exploited to create different formulations:

| Example No. | POE % | RESOMER® Select % |
|---|---|---|
| 4 | 6 | 94 |
| 5 | 15 | 85 |
| 6 | 30 | 70 |
| 7 | 50 | 50 |

The final polymer content (POE+RESOMERO) percentage was set at 5% w/w in ethyl acetate for all the following examples.

Example 4: Synthesis of 6% POE-PLGA Nanoparticles 0.05 g of the film made of 70 wt % POE and 30 wt % RESOMER® Select 7525 DLG 8E were dissolved together with 0.50 g of RESOMER® Select 7525 DLG 8E in ethyl acetate (52.22 mg mL$^{-1}$; 10.53 mL (=organic phase (OP)). This phase was joined with an aqueous phase (AP) containing polyvinyl alcohol (PVA; 20 mg mL$^{-1}$; 31.60 mL), directly in front of the sonication device using a T-junction at a flow rate of 2 mL/min and 6 mL/min, respectively. The mixture was then emulsified within the sonication device cooled to 14° C. at 100% amplitude to form a white, milky O/W-emulsion. The pressure of the transmitting fluid was 9 bar and the residence time of the mixture within the sonication field was 18.7 seconds. Directly after the sonication device, deionized water was introduced to the emulsion through a second T-junction at a flow rate of 61 mL/min and diluted the emulsion. During this step, ethyl acetate was extracted and the POE-PLG particles solidified. The nanoparticle suspension was then freeze-dried with addition of 3% trehalose as cryoprotectant. The particles were easily re-dispersible in water by gentle shaking.

| Particle size $D_z$ [nm] | PDI | Power Input [W/cm$^3$] |
|---|---|---|
| 141.8 | 0.077 | 32.5 |

Example 5: Synthesis of 15% POE-PLGA Nanoparticles 0.1 g of the film made of 70 wt % POE and 30 wt % 7525 DLG 8E were dissolved together with 0.37 g of RESOMER® Select 7525 DLG 8E in ethyl acetate (47.47 mg mL$^{-1}$; 9.83 mL (=organic phase (OP)). This phase was joined with an aqueous phase (AP) containing polyvinyl alcohol (PVA; 20 mg mL$^{-1}$; 29.49 mL), directly in front of the sonication device using a T-junction at a flow rate of 2 mL/min and 6 mL/min, respectively. The mixture was then emulsified within the sonication device cooled to 14° C. at 100% amplitude to form a white, milky O/W-emulsion. The pressure of the transmitting fluid was 9 bar and the residence time of the mixture within the sonication field was 18.7 seconds. Directly after the sonication device deionized water was introduced to the emulsion through a second T-junction at a flow rate of 61 mL/min and diluted the emulsion. During this step, ethyl acetate was extracted and the POE-PLG particles solidified. The nanoparticle suspension was then freeze-dried with addition of 3% trehalose as cryoprotectant. The particles were easily re-dispersible in water by gentle shaking.

| Particle size $D_z$ [nm] | PDI | Power Input [W/cm$^3$] |
|---|---|---|
| 142.37 | 0.069 | 31.3 |

Example 6: Synthesis of 30% POE-PLGA Nanoparticles 0.2 g of the film made of 70 wt % POE and 30 wt % 7525 DLG 8E were dissolved together with 0.27 g of RESOMER® Select 7525 DLG 8E in ethyl acetate (47.47 mg mL$^{-1}$; 9.83 mL (=organic phase (OP)). This phase was joined with an aqueous phase (AP) containing polyvinyl alcohol (PVA; 20 mg mL$^{-1}$; 29.49 mL), directly in front of the sonication device using a T-junction at a flow rate of 2 mL/min and 6 mL/min respectively. The mixture was then emulsified within the sonication device cooled to 14° C. at 100% amplitude to form a white, milky O/W-emulsion. The pressure of the transmitting fluid was 9 bar and the residence time of the mixture within the sonication field was 18.7 seconds. Directly after the sonication device deionized water was introduced to the emulsion through a second T-junction at a flow rate of 61 mL/min and diluted the emulsion. During this step, ethyl acetate was extracted and the POE-PLG particles solidified. The nanoparticle suspension was then freeze-dried with addition of 3% trehalose as cryoprotectant. The particles were easily re-dispersible in water by gentle shaking.

| Particle size D$_z$ [nm] | PDI | Power Input [W/cm$^3$] |
|---|---|---|
| 135.13 | 0.077 | 31.9 |

Example 7: Synthesis of 50% POE-PLGA Nanoparticles 0.31 g of the film made of 70 wt % POE and 30 wt % 7525 DLG 8E were dissolved together with 0.12 g of RESOMER® Select 7525 DLG 8E in ethyl acetate (47.47 mg mL$^{-1}$; 9.14 mL (=organic phase (OP)). This phase was joined with an aqueous phase (AP) containing polyvinyl alcohol (PVA; 20 mg mL$^{-1}$; 27.43 mL), directly in front of the sonication device using a T-junction at a flow rate of 2 mL/min and 6 mL/min, respectively. The mixture was then emulsified within the sonication device cooled to 14° C. at 100% amplitude to form a white, milky O/W-emulsion. The pressure of the transmitting fluid was 9 bar and the residence time of the mixture within the sonication field was 18.7 seconds. Directly after the sonication device deionized water was introduced to the emulsion through a second T-junction at a flow rate of 61 mL/min and diluted the emulsion. During this step, ethyl acetate was extracted and the POE-PLG particles solidified. The nanoparticle suspension was then freeze-dried with addition of 3% trehalose as cryoprotectant. The particles were easily re-dispersible in water by gentle shaking.

| Particle size D$_z$ [nm] | PDI | Power Input [W/cm$^3$] |
|---|---|---|
| 122.30 | 0.074 | 32.0 |

The invention claimed is:

1. A process for preparing nanoparticles by emulsion-solvent extraction or emulsion-solvent evaporation and application of ultrasonic sound, the process comprising:
    a) providing, in a first container, an organic phase (OP), comprising
        a first solvent or solvent mixture S1, comprising one or more organic solvent(s), and
        0.1 to 55% by weight of at least one bio-resorbable polyester,
    b) providing, in a second container, an aqueous phase (AP), comprising a second solvent or solvent mixture S2, comprising water, and an emulsion stabilizing agent,
    c) providing a stream of the organic phase (OP) and a stream of the aqueous phase (AP), and joining the stream of the organic phase (OP) and the stream of the aqueous phase (AP), into a joint stream,
    d) passing the joint stream through an ultrasonic sound flow-through cell under sonication with a power input of 20 to 50 W per cm$^3$ of the joint stream, to result in an emulsion appearing at an outlet of the ultrasonic sound flow-through cell,
    e) removing the first solvent or solvent mixture S1 and the second solvent or solvent mixture S2 by evaporation, or mixing the emulsion with an excess amount of an aqueous extraction phase (EP) to form a combined phase, resulting in removal of the first solvent or solvent mixture S1 from the emulsion; to form nanoparticles, and
    f) obtaining the nanoparticles comprising the at least one bio-resorbable polyester by concentration and drying the nanoparticles, to obtain a polymer powder with a Z-Average particle size D$_z$ in the range of 1 to 450 nm and with a polydispersity index PDI in the range of 0.01 to 0.5.

2. The process according to claim 1, wherein the organic phase (OP) comprises the first solvent or solvent mixture S1, which is not or only partially miscible with the second solvent or solvent mixture S2 of the aqueous phase (AP).

3. The process according to claim 1, wherein in d), the emulsion is an oil-in-water (O/W) emulsion.

4. The process according to claim 1, wherein in d), the emulsion is a water-in-oil (W$_1$/O) emulsion, which is, before e), mixed and emulsified with an additional water phase (W$_2$), to give a water-in-oil-in-water emulsion (W$_1$/O/W$_2$).

5. The process according to claim 2, wherein the first solvent or solvent mixture S1 comprises dichloromethane, ethyl acetate, chloroform, benzyl alcohol, diethyl carbonate, dimethyl sulfoxide, methanol, propylene carbonate, isopropyl acetate, methyl acetate, methyl ethyl ketone, butyl lactate, isovaleric acid, or any mixture thereof.

6. The process according to claim 1, wherein the second solvent or solvent mixture S2 comprises 60% or more and up to 100% by weight of water.

7. The process according to claim 1, wherein the second solvent or solvent mixture S2 is not or only partially miscible with the first solvent or solvent mixture S1, so that the aqueous phase (AP) and the organic phase (OP) form separate phases after mixing.

8. The process according to claim 1, wherein the aqueous phase (AP) comprises 0.1 to 10% by weight of the emulsion stabilizing agent.

9. The process according to claim 1, wherein the aqueous extraction phase (EP) comprises 80% by weight or more of water.

10. The process according to claim 1, wherein the at least one bio-resorbable polyester is selected from the group consisting of a polyorthoester, a polylactide, a polydioxanone, a polycaprolactone, a polytrimethyl carbonate, a polyglycolide, a poly(lactide-co-glycolide), a poly(lactide-co-caprolactone), a poly(lactide-co-trimethyl carbonate), a poly(lactide-co-polyethylene-glycol), and any blend thereof.

11. The process according to claim 1, wherein the organic phase (OP) or the aqueous phase (AP) or both comprise(s) an active pharmaceutical ingredient.

12. The process according to claim 1, wherein in c), the stream of the organic phase (OP) is provided at a flow rate of 0.5 to 50 ml/min, and the stream of the aqueous phase (AP) is provided at allow rate of 1.5 to 150 ml/min, with the proviso that the flow rate of the aqueous phase (AP) is higher than the flow rate of the organic phase (OP), resulting in an oil-in-water emulsion (O/W) in d).

13. The process according to claim 1, wherein in c), the stream of the organic phase (OP) is provided at a flow rate of 1.5 to 150 ml/min, and the stream of the aqueous phase (AP) is provided at a flow rate of 0.5 to 50 ml/min, with the proviso that the flow rate of the organic phase (OP) is higher than the flow rate of the aqueous phase (AP), resulting in a water-in-oil emulsion ($W_1$/O) in d).

14. The process according to claim 1, wherein a residence time of the joint stream in the ultrasonic sound flow-through cell is from 0.5 to 80 seconds.

15. The process according to claim 1, wherein a flow rate of the joint stream in the ultrasonic sound flow-through cell is from 2 to 200 ml/min.

16. The process according to claim 4, wherein the water-in-oil ($W_1$/O) emulsion is mixed and emulsified with the additional water phase ($W_2$) by a static mixer or a further sonication flow-through cell.

17. The process according to claim 8, wherein the emulsion stabilizing agent is polyvinyl alcohol or polysorbate.

18. The process according to claim 1, wherein a power input is 27 to 45 W per $cm^3$.

19. The process according to claim 1, wherein said polymer powder with a Z-Average particle size $D_z$ in the range of 50 to 200 nm.

20. The process according to claim 1, wherein the first solvent or solvent mixture S1 comprises dichloromethane, ethyl acetate, chloroform, benzyl alcohol, diethyl carbonate, propylene carbonate, isopropyl acetate, methyl acetate, methyl ethyl ketone, butyl lactate, isovaleric acid, or any mixture thereof.

21. The process according to claim 1, wherein a power input is 27 to 50 W per $cm^3$.

* * * * *